(12) United States Patent
Karadeniz

(10) Patent No.: US 10,561,457 B2
(45) Date of Patent: Feb. 18, 2020

(54) WIRE STRETCHER FOR KIRSCHNER WIRE PASSING THROUGH WIRE RETAINERS

(71) Applicant: Emre Karadeniz, Istanbul (TR)

(72) Inventor: Emre Karadeniz, Istanbul (TR)

( * ) Notice: Subject to any disclaimer, the term of this patent is extended or adjusted under 35 U.S.C. 154(b) by 281 days.

(21) Appl. No.: 15/558,040

(22) PCT Filed: Mar. 17, 2015

(86) PCT No.: PCT/TR2015/000109
§ 371 (c)(1),
(2) Date: Sep. 13, 2017

(87) PCT Pub. No.: WO2016/148662
PCT Pub. Date: Sep. 22, 2016

(65) Prior Publication Data
US 2018/0064473 A1    Mar. 8, 2018

(51) Int. Cl.
*A61B 17/88* (2006.01)
*A61B 17/84* (2006.01)
(52) U.S. Cl.
CPC ........ *A61B 17/8861* (2013.01); *A61B 17/848* (2013.01); *A61B 17/8869* (2013.01)
(58) Field of Classification Search
CPC ..... A61B 17/84; A61B 17/842; A61B 17/846; A61B 17/848; A61B 17/8861; A61B 17/8869; A61B 17/8897
See application file for complete search history.

(56) References Cited

U.S. PATENT DOCUMENTS

| | | | |
|---|---|---|---|
| 3,387,417 A | | 6/1968 | Howlett |
| 6,053,921 A | * | 4/2000 | Wagner .................. A61B 17/82 606/103 |
| 6,378,289 B1 | * | 4/2002 | Trudeau ............. A61B 17/8861 24/134 R |
| 8,632,551 B2 | | 1/2014 | Schwer et al. |
| 8,984,720 B2 | * | 3/2015 | Gephart ............. A61B 17/8861 24/69 R |
| 10,314,635 B2 | * | 6/2019 | Gephart ............. A61B 17/8869 |
| 2010/0042106 A1 | * | 2/2010 | Bryant ............... A61B 17/8869 606/103 |
| 2010/0106194 A1 | * | 4/2010 | Bonutti .............. A61B 17/0218 606/279 |

(Continued)

FOREIGN PATENT DOCUMENTS

JP    2005065748 A    3/2005

OTHER PUBLICATIONS

International Search Report for corresponding International Application No. PCT/TR2015/000109.

*Primary Examiner* — Eric S Gibson
(74) *Attorney, Agent, or Firm* — Egbert, McDaniel & Swartz, PLLC

(57) ABSTRACT

Provided is a wire stretcher, which is an apparatus which compresses the portion of the k-wire getting out behind the squeezing apparatus, the k-wire being passed through the wire retainer fitted on the bone surface, by rotating the holding part subsequent to being passed through the wire stretcher, thanks to the k-wire channel therein, and which enables, by rotating the outer body, the inner body with which the compressed k-wire is connected and the mid body to advance together in direction X, thereby stretching the k-wire.

6 Claims, 5 Drawing Sheets

(56) References Cited

U.S. PATENT DOCUMENTS

| | | | |
|---|---|---|---|
| 2010/0318137 A1* | 12/2010 | Stucki | A61B 17/8066 606/324 |
| 2011/0112537 A1* | 5/2011 | Bernstein | A61B 17/8869 606/74 |
| 2013/0167334 A1* | 7/2013 | Gephart | A61B 17/8861 24/69 R |
| 2015/0342654 A1* | 12/2015 | Gephart | A61B 17/8869 606/74 |
| 2017/0209190 A1* | 7/2017 | Goodwin, Jr. | A61B 17/8004 |
| 2018/0064473 A1* | 3/2018 | Karadeniz | A61B 17/7083 |
| 2018/0132920 A1* | 5/2018 | Vikinsky | A61B 17/8875 |
| 2019/0133655 A1* | 5/2019 | Bonutti | A61B 17/842 |

* cited by examiner

WIRE STRETCHER FOR KIRSCHNER WIRE PASSING THROUGH WIRE RETAINERS

TECHNICAL FIELD

The invention is particularly related to an apparatus which allows the Kirschner wire having been secured formerly to be stretched, and thus provides compression by stretching the wire at the distance between the two wire retainers used for fastening, subsequent to pushing the wire retainers, which secure the Kirschner wire used for fastening and treating the fractured bones by being passed through the bones, until the bone surface, and placing them on the bone surface in the field of orthopedic surgery.

STATE OF THE ART

Techniques developed for surgical treatment of fractures so far are Kirschner wire (k-wire), screw, plate-screw, intramedullary nail and external fastening. The purpose of such techniques is to hold the fractured bone pieces in the desired position until fracture healing. The advantages and disadvantages of these techniques vary according to the type of fracture and they shape the treatment plan of the surgeon.

Among these techniques, in the technique of fastening with k-wire, after setting (reducing) the broken bones, these straight wires are made to pass between the bone pieces, whereby the broken bones are fastened. After reduction, fractured bone pieces may move back and forth through the wire since the wires cannot provide compression between fractured bone pieces. In addition, these wires may also move after being placed into the body.

In fastening the broken bones with screw, the fractured bone pieces are placed into their original places first. Compression between the pieces is obtained according to the principle of forming mutual force between the screw head and the screw threads, which is the working principle of screw. In this technique, it is required to increase the dimensions of the screw in order to increase the attachment and compression force between the pieces. However, if the bone pieces are small in size, the dimension of the screw cannot be increased. Due to the screw dimension, there may be no space left to locate an additional screw between the pieces. Moreover, as a surgical technique, first the bone is drilled with a drill, and then grooves are opened for screw threads (tapering), subsequent to which the screw is located. Additionally, prior to these processes, sometimes k-wire is needed to be placed to guide the screw. As a result, the surgical technique is relatively difficult. Moreover, the attachment intended to be provided by screw threads is not practical for patients with osteoporosis.

On the other hand, in fastening the fractured bones with plate screw, fractured bone pieces are secured to their locations by plates held by screws, subsequent to reduction. However, since the plates are held by screws, all of the disadvantages of screw technique are also experienced herein. The process of placing plates requires abrading more tissue surrounding the bone. This, in turn, means more incision and more nutrition problem for the bone pieces. The plate may prevent the healing of skin where the under skin tissue is very thin and may be felt by hand. When the bone pieces are too small or too close to the joints, it becomes impossible to place the plates. Furthermore, when the plates are to be taken out, the surrounding tissues are damaged again.

As a consequence, due to the aforementioned disadvantages and the insufficiency of the existing solutions regarding the subject matter, the product with the Application No. 2010/05662 titled "A wire retainer" has been developed, as distinct from the known methods. The wire stretcher according to the present application has been developed so as to succeed in the use of this "wire retainer" for fastening of the fractured bones.

OBJECTS OF THE INVENTION

The main object of the invention is to provide an apparatus for stretching the k-wire passing through the retainer, after placing the "Wire retainers", the subject matter of an examined patent, into the body without damaging the tissues during surgery so that fracture healing process can be accelerated.

The object of the invention is to heal the fractured bones by giving minimum harm to the bones and the surrounding soft tissues by way of using the wire retainers with percutaneous techniques.

An object of the invention is to allow for fastening after reduction by means of thin wires by providing compression at the fracture line, and thus to make it possible to compress tiny fractured bone pieces.

An object of the invention is to permit the use of thin k-wires for both compression and support purposes by the virtue of "A wire retainer".

Another object of the invention is to eliminate the important problem of "penetrating of small parts" in fractures in the vicinity of the joints, e.g. knees, by allowing the use thereof for treatment.

Thick grooves are opened on the bone pieces so as to place the screw. An object of the invention is to minimize the problem of formation of new fractures due to these thick grooves by the usage of k-wires, which are much thinner than these grooves.

Another object of the invention is to allow for providing compression over the wire by using the same along with "A wire retainer" according to the Application No. 2010/05662 in cases where the bone anatomy does not allow the usage of thick fastening elements, as in the case of fractures around the elbow.

And another object of the invention is to perform the surgery without requiring such processes as tapering and drilling.

The structural and distinctive characteristics and all advantages of the invention will be better understood with the figures below and the detailed description written by referring to these figures; therefore, the invention should be evaluated by taking these figures and the detailed explanations into account.

FIGURES FOR A BETTER UNDERSTANDING OF THE INVENTION

DESCRIPTION OF THE REFERENCES

WS. Wire Stretcher
G. Gripper
R. Retainer
S. Squeezing Apparatus
C. Working Cannula
1. Formed Tip
2. K-wire Channel
3. Outer Body
4. Inner Body
5. Holding Part
6. Kirschner wire K-wire
7. Mid body
8. Moving threads
9. Lower Part
10. Upper Part The drawings do not necessarily need to be scaled and the details that are not required for understanding the present invention may have been ignored. Apart from that, the components that are at least substantially identical or have at least substantially identical functions are referred with the same numeral.

DETAILED DESCRIPTION OF THE INVENTION

In this detailed description, the preferred embodiments of the wire stretcher (WS) according to the invention are described only for a better understanding of the subject matter.

The applications of the working cannula, gripper, and the squeezing apparatus, which are mentioned in the embodiment of the present invention, have all been made by us.

Figure 1:
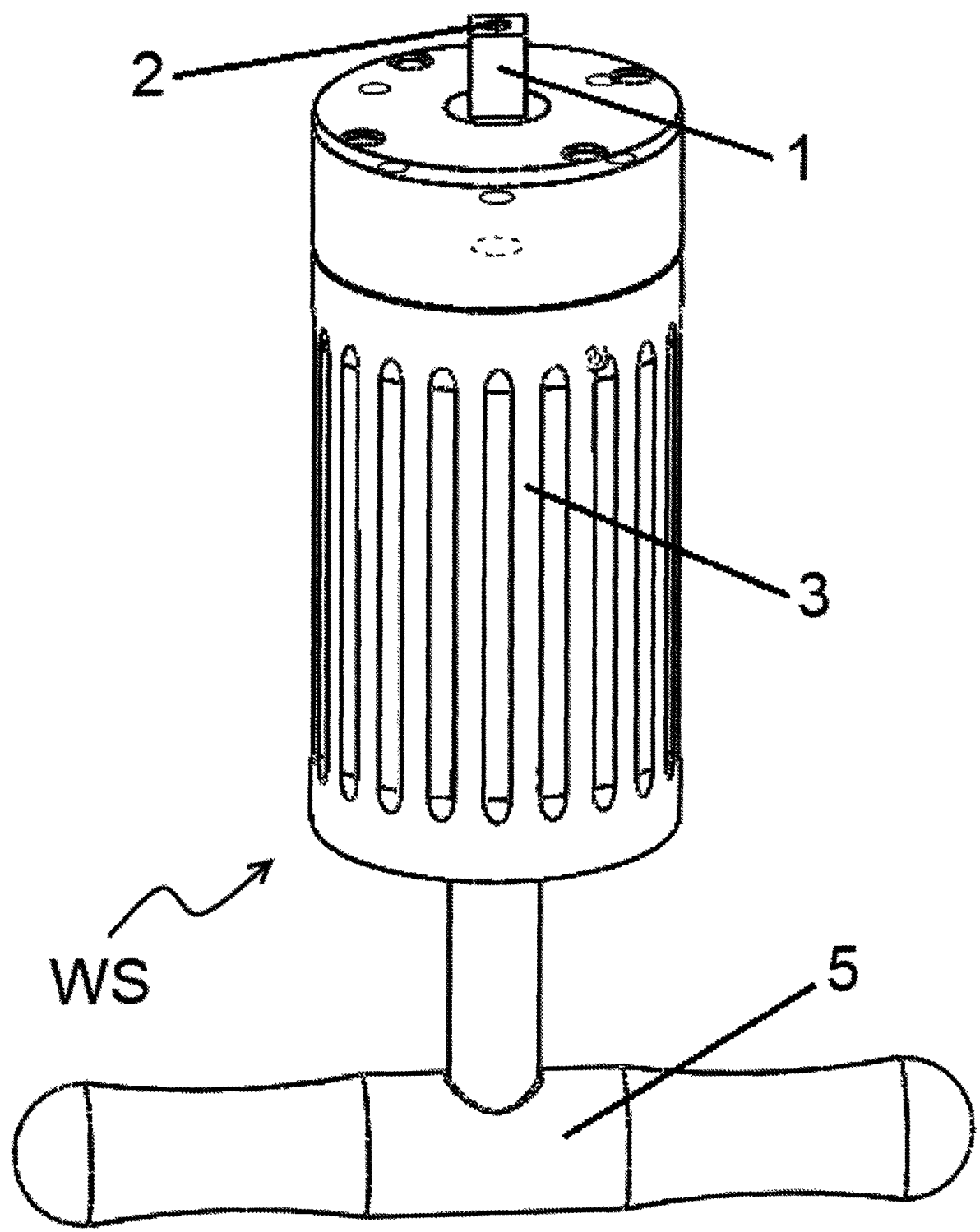
FIG. 1 is the overall view of the wire stretcher according to the invention.

As shown in FIG. 1, the working cannula (C) is an apparatus which
comprises a knurled tip which abrades the bone tissue of the soft tissues thereon, allows advancing without cutting the surrounding tissues, is formed in compliance with the diameter of the wire retainer (R), and has protrusions and recesses
and constitutes a working corridor for various surgical apparatuses.

The squeezing apparatus is a component which comprises a formed tip which is seated in the grooves in the upper part (5) of the retainer (R) by passing there through; and which tightens—locks or loosens—removes the retainer (R) on the bone surface by rotating the screw system of the retainer (R).

The gripper is a component which comprises a formed tip which prevents the release of the retainer (R) by passing through the working cannula (C) and which is formed in accordance with the shape of the retainer (R) in order to fully contact with the wire retainer (R).

The present invention is used together with "A wire retainer" according to the Application No. 2010/05662, which has been granted an examined patent certificate by Turkish Patent Institute and which is used for fastening the broken bones. Said wire stretcher (WS) especially allows the k-wire (6) passing through the retainer (R) by being seated in the bearing disposed in the holding part of the squeezing apparatus (S), after the squeezing apparatus (S) which is connected with the retainer (R) by passing through the working cannula (C) compresses the retainer (R) on the bone surface, subsequent to placing the retainer (R) according to the Application No. 2010/05662 onto the bone surface by being passed through the working corridor formed by the working cannula (C) by means of the gripper (G) via percutaneous techniques.

The wire stretcher (WS) comprises;
 a formed tip (1) which is seated in a bearing formed at the outlet/opening of the k-wire channel belonging to the squeezing apparatus and is disposed in the holding part of the squeezing apparatus (S);
 a k-wire channel (2) which allows the squeezing apparatus (S) to advance over the k-wire (6) until being seated in the groove formed in the holding part and extends along the entire apparatus (starting from the formed tip (1), continuing along the inner body (4), and ending in the holding part (5));
 a holding part (5) which allows the use to be directed manually;
 an inner body (4), a mid body (7) accommodating the inner body (4), and an outer body (3) accommodating the mid body (7); and
 moveable threads (8) which are disposed at the end of the inner body (4) which is in fixed connection with the holding part (5); which allow the k-wire (6) to pass there through by being widened when the holding part (5) is rotated counterclockwise and opened; and which compress the k-wire (6) by getting close to one another upon clockwise rotation of the outer body (3) after the k-wire (6) passes through the k-wire channel (2).

Since the dimensions of "A wire retainer" are equal to the size of screw heads, the retainer (R) occupies less space compared to the plates located onto the broken bones and the problem of feeling the retainer (R) under the skin with hand is less experienced. Because the compression force provided by threads in screws requires attachment to the bone marrow; the usage thereof causes difficulties in patients with low bone quality. However, as "A wire retainer" provides attachment over the bone cortex, it provides very important advantages in terms of use in patients with low bone quality, e.g. patients with osteoporosis. Since cortical attachment is provided by "A wire retainer", the problem of dislocation of retainers (R) is eliminated.

Figure 4:
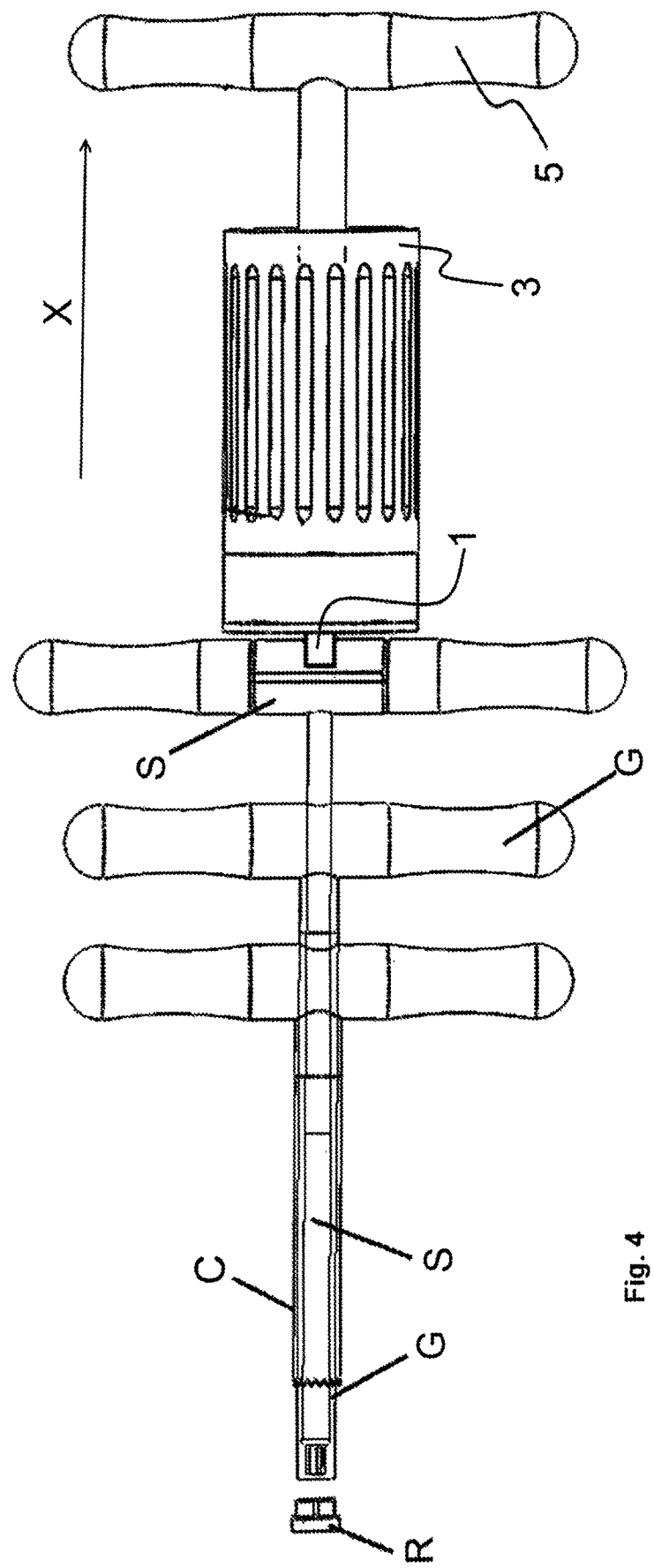
FIG. 4 is the view of the use of the wire stretcher according to the invention together with the working cannula, gripper, and screwdriver.

The wire stretcher (WS) has been developed for stretching the k-wire (6) in the position it assumed, and thus providing compression in the fracture line, after the retainer (R) according to the patent titled "A wire retainer" is placed properly at the desired position on the bone (FIG. 4). In other words, compressing the wire by means of the wire stretcher (WS) after the wire retainers (R) rest on the bone cortex causes the wire retainers (R) to push the bone cortex into which they are fitted, and thus the part to compress the fracture line.

Figure 2:
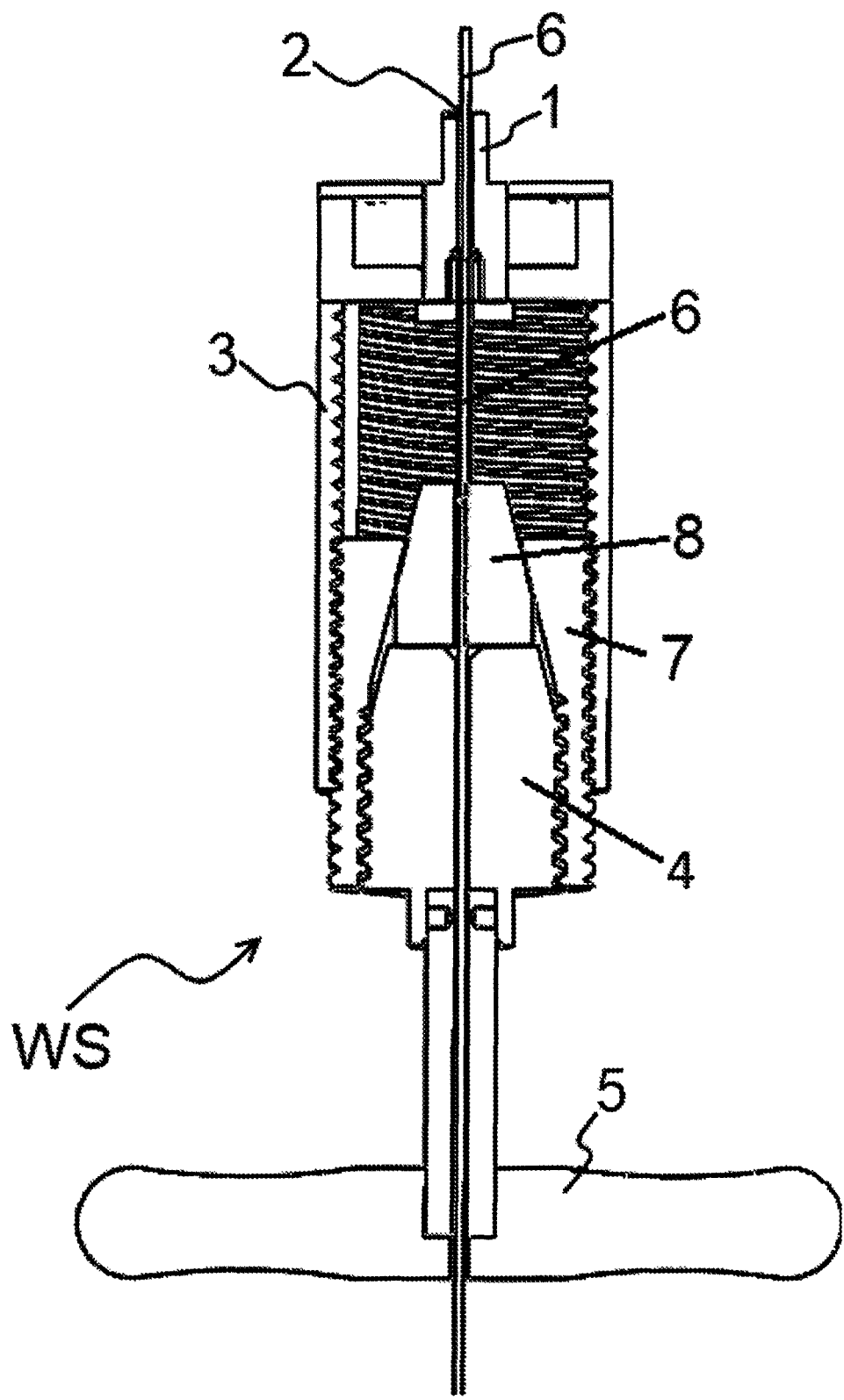
FIG. 2 is the overall view of the wire stretcher according to the invention from another angle.
Figure 3:
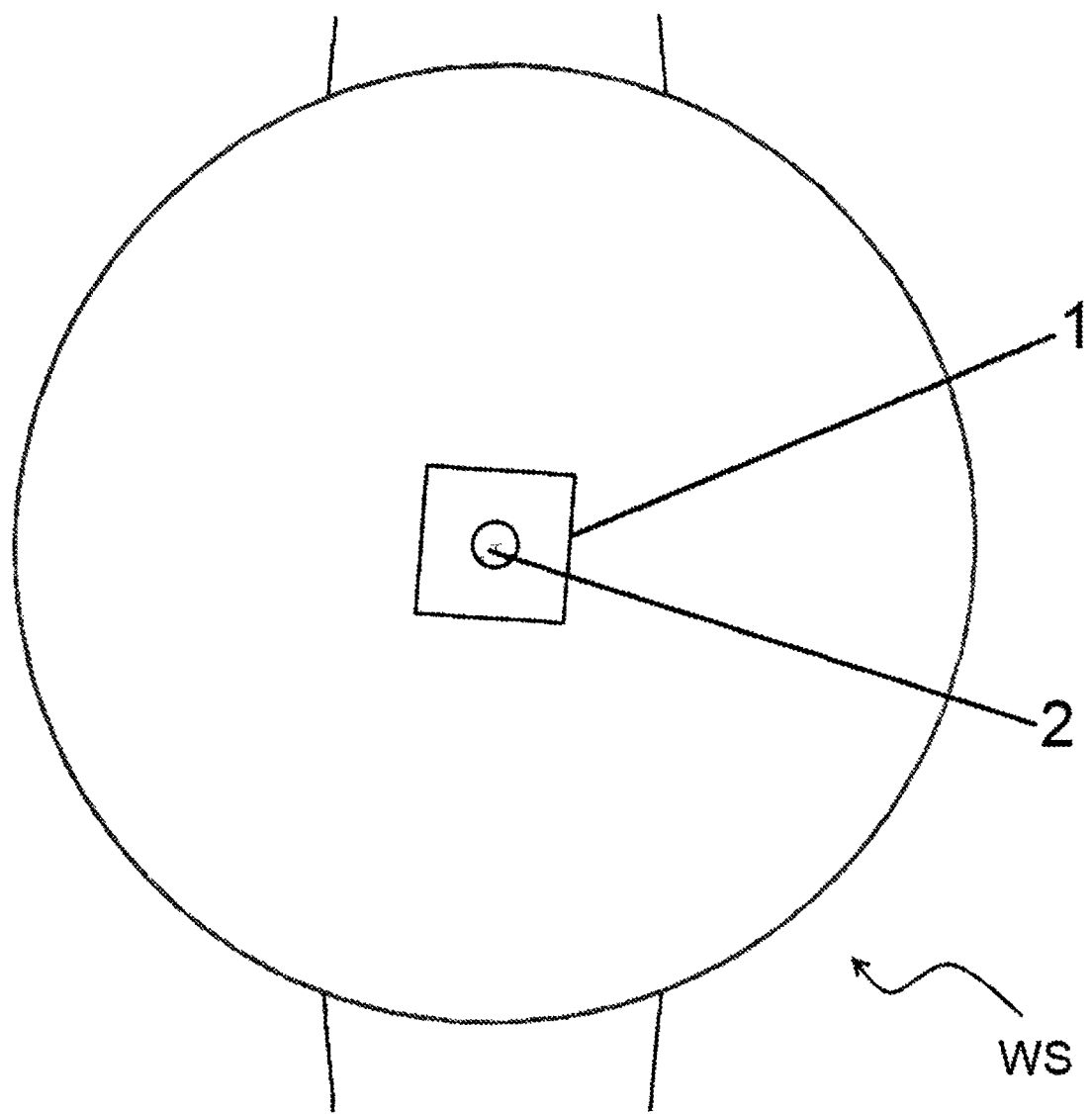
FIG. 3 is the detailed/close-up view of the tip part of the wire stretcher according to the invention.

Thanks to the k-wire channel (2) disposed in the wire stretcher (WS), the portion of the k-wire (6) getting out behind the squeezing apparatus (S) is passed through the wire stretcher (WS). The formed tip (1) is formed in a way to be suited for the groove/bearing which is disposed in the holding part of the squeezing apparatus (S) and out of which the k-wire (6) gets (FIG. 2). This form allows the wire stretcher (WS) to properly fit onto the squeezing apparatus (S). The inner body (4) where the moveable threads (8) are located is formed in a narrowing down configuration towards the formed tip (1) (in a funnel-like manner). Hence, when the holding part (5) which is directly connected with the inner body (4) is rotated clockwise, the moveable threads (8) advance towards the narrow portion of the inner body (4) and get closer to one another towards the k-wire channel (2). The k-wire (6) is thus compressed. (When the holding part (5) which is directly connected with the inner body (4) is rotated counterclockwise, the moveable threads (8) retract to the wider portion of the inner body (4) and get away from one another and from the k-wire channel (2).) Upon rotating the outer body (3) clockwise when the k-wire (6) is compressed, the mid body (7) and the inner body (4) together retract in direction X (towards the holding part (5)) inside the outer body (3) (FIG. 4). The k-wire (6) is stretched and the wire retainer (R) at the tip of the squeezing apparatus (S) advances slightly on the k-wire (6) so as to apply compression on the fractured bone. Thus, the wire stretcher (WS) provides compression in the fracture line by means of stretching the k-wire (6) which is held firmly inside the inner body (4).

Figure 5:
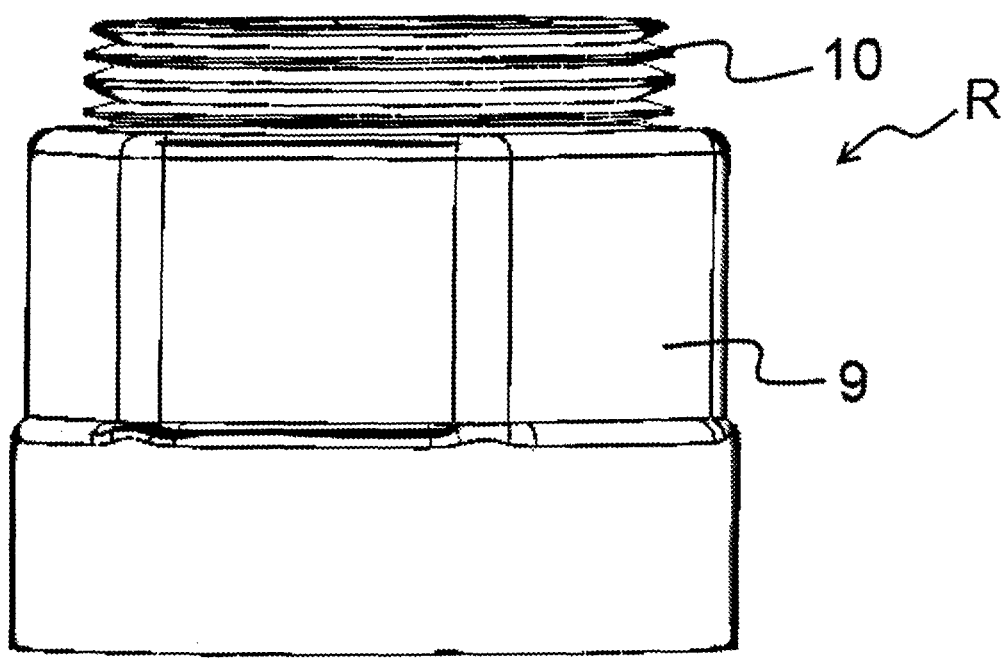
FIG. 5 is the overall view of the wire retainer in an alternative embodiment where the upper part is male and the lower part is female.

Subsequent to stretching operation, the upper part (10) is compressed on the lower part (9) by the squeezing apparatus (S), thereby locking the wire retainer (R) therein (FIG. 5).

In an Alternative Embodiment of the Invention

The formed tip (1) of the invention is configured in a suitable way to the groove/bearing form at the top of the squeezing apparatus (S). This form can be triangle, rectangle, or have another shape.

The k-wire channel (2) which is at the center of the inner body (4), and thus at the center of the mid body (7) and of the outer body (3) as well, and extends all along the outer body (3) (i.e. follows it along the wire stretcher (WS)) may have a different diameter, or be placed eccentrically.

The bodies of the invention may have a shape other than cylinder (e.g. hexagonal, rectangle) and a different length. The holding part (5) of the invention may be "T", "L", "C" shaped or may have another shape.

The invention claimed is:

1. A wire stretcher that allows a retainer to advance over a k-wire in order for the retainer to apply compression onto a fractured bone by stretching the k-wire prior to placing the retainer at a desired area of a surface of the fractured bone, the wire stretcher comprising
   an outer body;
   a mid body positioned inside said outer body;
   an inner body positioned inside said mid body, said inner body having a k-wire channel at a center thereof;
   a formed tip located at one end of said outer body, said formed tip adapted to connect to the retainer;
   a squeezing apparatus having a k-wire channel and a bearing formed at an outlet of the k-wire channel, said formed tip suited for the bearing, said k-wire channel of said inner body adapted to allow the wire stretcher to advance over the k-wire until said formed tip and the bearing fully contact each other;
   a holding part fixedly connected to said inner body and adapted to allow manual guidance of the stretching; and
   a plurality of movable threads adapted to allow the k-wire to pass there through while compressing the k-wire after the k-wire passes through the k-wire channel of said inner body, said inner body and said mid body being movable upon rotation of said outer body so as to stretch the k-wire.

2. The wire stretcher of claim 1, wherein said holding part is in fixed connection with said inner body.

3. The wire stretcher of claim 2, wherein said inner body is rotatable inside said mid body, said outer body being rotatable along an outer surface of said mid body.

4. The wire stretcher of claim 3, wherein said plurality of movable threads are opened when said holding part is rotated counterclockwise such that the k-wire can pass through the k-wire channel of said inner body, said plurality of movable threads being closed when said holding part is rotated clockwise so as to compress the k-wire, said plurality of movable threads being directly connected to said inner body.

5. The wire stretcher of claim 4, wherein said plurality of movable threads retract together with said holding part so as to approach a wide rear portion of said inner body and to widen the k-wire channel of said inner body when said holding part is rotated counterclockwise, wherein said plurality of movable threads advance in a direction of said formed tip towards a narrow portion of said inner body so as to get close to one another toward the k-wire channel of said inner body so as to compress the k-wire when said holding part is rotated clockwise.

6. The wire stretcher of claim 3, wherein said inner body has threads of said plurality of movable threads on a surface that contacts said mid body such that said inner body can rotate inside said mid body when said holding part is rotated, said mid body having thread bearings suited for the threads, said mid body having the threads of said plurality of movable threads on a surface that contacts said outer body, said mid body having additional thread bearings suited for threads of said plurality of movable threads on a surface of said outer body that contacts said mid body upon being rotated clockwise so that said inner body and said mid body can move together towards said holding part so as to stretch the k-wire.

* * * * *